United States Patent
Locke et al.

(10) Patent No.: US 12,076,217 B2
(45) Date of Patent: Sep. 3, 2024

(54) SYSTEMS AND METHODS FOR TRAUMA-FREE APPLICATION AND REMOVAL OF LIGHT DEACTIVATED ADHESIVE DRAPES

(71) Applicant: Solventum Intellectual Properties Company, Maplewood, MN (US)

(72) Inventors: Christopher Brian Locke, Blandford Forum (GB); David Whyte, Wareham (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 973 days.

(21) Appl. No.: 16/970,788

(22) PCT Filed: Feb. 18, 2019

(86) PCT No.: PCT/US2019/018386
§ 371 (c)(1),
(2) Date: Aug. 18, 2020

(87) PCT Pub. No.: WO2019/161321
PCT Pub. Date: Aug. 22, 2019

(65) Prior Publication Data
US 2020/0368075 A1   Nov. 26, 2020

Related U.S. Application Data

(60) Provisional application No. 62/632,176, filed on Feb. 19, 2018.

(51) Int. Cl.
*A61F 13/02*   (2024.01)
*A61B 46/20*   (2016.01)
(Continued)

(52) U.S. Cl.
CPC .......... *A61F 13/0266* (2013.01); *A61B 46/20* (2016.02); *A61F 13/0206* (2013.01);
(Continued)

(58) Field of Classification Search
CPC .............. A61F 13/0266; A61F 13/0206; A61F 13/0253; A61F 13/0269;
(Continued)

(56) References Cited

U.S. PATENT DOCUMENTS 5,891,077 A * 4/1999 Gilman ................. A61F 13/025
602/44
7,563,941 B2 † 7/2009 Lebner
(Continued)

FOREIGN PATENT DOCUMENTS

WO   WO 1999/018136   4/1999
WO   WO 2014/202935   12/2014
(Continued)

OTHER PUBLICATIONS

International Search Report and Written Opinon issued in Corresponding PCT Application No. PCT/US2019/018386, dated May 13, 2019.

*Primary Examiner* — Leslie A Lopez
*Assistant Examiner* — Katherine-Ph Minh Pham (57) ABSTRACT

Provided herein is a system and method for trauma-free application and removal of light deactivated adhesive drapes. One aspect provides a system comprising a drape, at least one photosensitive adhesive portion having a release agent, and at least one acrylic and/or polyurethane adhesive portion, where the system is adapted to be coupled to a tissue site and released therefrom upon or after exposure to an external stimulus such as certain wavelengths of light. The system may have a removable blocking layer to prevent the photosensitive adhesive from being exposed to deactivation (Continued)

wavelengths prematurely. Another aspect provides a method for application and removal of a drape using by removing the removable blocking layer and applying light to the drape to deactivate the photosensitive adhesive portion and promote easy, clean, and less painful removal of the drape. When the photosensitive adhesive portion is deactivated, the acrylic and/or polyurethane adhesive portion maintains adhesion between the drape and the tissue until removal of the drape.

14 Claims, 8 Drawing Sheets

(51) Int. Cl.
*A61F 13/00* (2024.01)
*A61F 13/0206* (2024.01)
*A61F 13/0246* (2024.01)
(52) U.S. Cl.
CPC ...... *A61F 13/0253* (2013.01); *A61F 13/0269* (2013.01); *A61B 2046/205* (2016.02); *A61F 2013/00182* (2013.01); *A61F 2013/00246* (2013.01); *A61F 2013/00289* (2013.01)
(58) Field of Classification Search
CPC .. A61F 2013/00182; A61F 2013/00246; A61F 2013/00289; A61F 13/025; A61F 13/0246; A61B 46/20; A61B 2046/205
See application file for complete search history.

(56) References Cited

U.S. PATENT DOCUMENTS

| | | | |
|---|---|---|---|
| 8,697,932 B2* | 4/2014 | Tunius | A61L 15/585 602/41 |
| 2003/0165686 A1* | 9/2003 | Blackburn | G02B 5/23 428/423.1 |
| 2008/0090726 A1* | 4/2008 | Eskra | B41M 5/385 503/207 |
| 2009/0216170 A1 | 8/2009 | Robinson et al. | |
| 2009/0312685 A1* | 12/2009 | Olsen | A61F 13/0269 604/386 |
| 2014/0155791 A1* | 6/2014 | Robinson | A61F 13/023 601/7 |
| 2015/0245949 A1† | 9/2015 | Locke | |
| 2015/0315423 A1† | 11/2015 | Park | |
| 2016/0030250 A1* | 2/2016 | Caneppele | A61F 13/0259 602/56 |
| 2018/0042789 A1* | 2/2018 | Bradford | A61F 13/0259 |

FOREIGN PATENT DOCUMENTS

WO 2015/132551 A1 † 9/2015
WO WO 2015/175963 11/2015
WO WO 2016/124339 8/2016

\* cited by examiner
† cited by third party

SYSTEMS AND METHODS FOR TRAUMA-FREE APPLICATION AND REMOVAL OF LIGHT DEACTIVATED ADHESIVE DRAPES

CROSS-REFERENCE TO RELATED APPLICATIONS

This application is a national phase application under 35 U.S.C. § 371 of International Application No. PCT/US2019/018386, filed Feb. 18, 2019, which claims priority to and the benefit of U.S. Provisional Application No. 62/632,176, filed Feb. 19, 2018, the entire contents of which are incorporated in to the present application by reference in their entirety.

BACKGROUND

1. Technical Field

The present application relates generally to the field of tissue treatment, and more specifically to a system and method for facilitating the application and removal of a drape from a tissue site.

2. Description of Related Art

Systems and devices currently exist for the treatment of tissue, such as wound tissue and skin tissue. Some current tissue treatment systems require the use of an adhesive drape to secure all or a portion of the tissue treatment system to a tissue site. For example, an adhesive drape can be used to secure a gauze portion of a bandage to a wound site by adhering to the skin or other tissue surrounding the wound. Drapes intended for use with negative pressure wound therapy (NPWT) have certain desirable characteristics. Some of these characteristics are that the drape is easy to apply, doesn't adhere well to itself if folded (e.g., adhesive to adhesive) upon application to tissue, achieves a good seal with the tissue, adheres well to tissue and to its film (e.g., polyurethane) covering when layered or overlapped, enables atraumatic removal, is highly breathable, is repositionable upon application, and achieves adhesion that is not affected by patient heat or sweat.

One example of a commonly used drape system is an advanced wound dressing (AWD). A challenge with bordered AWDs is to get a balance of adhesive strength vs. trauma upon removal at the optimum point for a wide range of users and skin types. AWDs are used on a wide range of chronic wounds and thus on a wide range of patients, some of whom have delicate and friable skin and others who have a high degree of sensitivity to pain. If the adhesive is insufficiently strong, the adhesive can give way during wear and result in fluid leaks which can be distressing for the patient, or the dressing can come away from the patient. If the adhesive is too aggressive, it can be painful upon removal and result in skin-stripping. Silicones and other adhesives have been used to try to reduce trauma; however, these can lack bond strength and can be adversely affected by moisture. Therefore, a strong adhesive drape is needed which maintains adhesion during the length of the wound therapy but does not result in any trauma to the tissue when the dressing is removed.

SUMMARY

Disclosed are various exemplary embodiments of systems and methods for trauma-free application and removal of light deactivated adhesive drapes. Some embodiments disclose a bordered AWD design and construction that can integrate a light-switchable adhesive layer within it designed to provide for trauma-free removal. In some embodiments, a light deactivated adhesive drape system is configured to be coupled to tissue, the system comprising: a drape comprising: an absorbent portion configured to contact a wound on the tissue; at least one photosensitive adhesive portion configured to adhere to the tissue and having at least one release agent disposed within the adhesive layer, wherein the at least one release agent is configured to weaken a bond of the adhesive layer to the tissue upon exposure to at least one of a plurality of light wavelengths; and at least one acrylic and/or polyurethane adhesive portion configured to adhere to the tissue, the adhesion of the at least one acrylic adhesive portion having an adhesion less than the at least one photosensitive adhesive portion in an activated state and greater than the at least one photosensitive adhesive portion in a deactivated state, wherein the at least one acrylic and/or polyurethane adhesive portion maintains adhesion to the tissue upon exposure to the at least one of a plurality of light wavelengths.

In some embodiments, the drape further comprises a drape cover disposed over the absorbent portion, the drape cover including: a thin, flexible, and breathable film layer; and an adhesive layer disposed on an underside of the film layer, the adhesive layer including the at least one photosensitive adhesive portion and the at least one acrylic and/or polyurethane adhesive portion. In some embodiments, the drape further comprises a removable blocking layer configured to block the plurality of light wavelengths that activate the at least one release agent, wherein the plurality of light wavelengths are wavelengths comprising a portion of the visible light spectrum. In some embodiments, the drape further comprises a removable release layer disposed on an underside of the drape and configured to cover the adhesive layer. In some embodiments, the absorbent portion is disposed in a central area of the drape and comprises one or more of a hydrophilic foam, foam and absorbent laminate, algenate, hydro-polymer, textile, non-woven polymer, and bio-polymer. In some embodiments, the thin, flexible, and breathable film layer comprises a material having a moderate to high moisture vapor transmission rate (MVTR). In some embodiments, the thin, flexible, and breathable film layer is disposed on top of the absorbent portion and the adhesive layer and extends across the entire surface area of the drape. In some embodiments, the adhesive layer is pattern printed to have adhesive areas and non-adhesive areas. In some embodiments, one of the non-adhesive areas covers the absorbent portion and the adhesive areas completely surround the absorbent portion. In some embodiments, the drape cover is configured to enable the plurality of light wavelengths to pass through the drape cover and contact the at least one photosensitive adhesive portion. In some embodiments, the drape cover is a optically transparent.

In some embodiments, the removable blocking layer comprises a material having a high MVTR. In some embodiments, the removable blocking layer includes an adhesive having a bond strength enabling it to be removed with an application of 1-2 N of force. In some embodiments, the removable blocking layer covers the top of the adhesive layer. In some embodiments, the removable blocking layer covers the top of the adhesive layer and the absorbent layer. In some embodiments, the removable blocking layer includes an indication to a user of the drape that the removable blocking layer should be removed when deactivation of the at least one photosensitive adhesive portion is desired. In some embodiments, the at least one photosensitive adhesive portion is disposed inboard of both the absorbent layer and the outer edges of the drape. In some embodiments, the at least one photosensitive adhesive portion is separated from the absorbent layer and the outer edges of the drape by the at least one acrylic and/or polyurethane adhesive portion. In some embodiments, the at least one acrylic and/or polyurethane adhesive portion is not disposed at one or more of the corners of the drape. In some embodiments, the drape includes an indication to a user of the drape that the at least one photosensitive adhesive portion is deactivated upon exposure to the at least one of a plurality of light wavelengths. In some embodiments, the indication is a light sensitive dye that changes color, state, or design upon deactivation of the at least one photosensitive adhesive portion. In some embodiments, the ratio of the at least one photosensitive adhesive portion and the at least one acrylic and/or polyurethane adhesive portion disposed in the adhesive layer is 80:20. In some embodiments, the at least one photosensitive adhesive portion extends to the outer edges of the drape and is perforated by a plurality of acrylic and/or polyurethane adhesive portions. In some embodiments, the plurality of acrylic and/or polyurethane adhesive portions are not covered by the removable blocking layer. In some embodiments, the plurality of acrylic and/or polyurethane adhesive portions are covered by the removable blocking layer. In some embodiments, the removable blocking layer includes one or more of a printed layer, a coated dye layer, and a particulate layer. In some embodiments, the removable blocking layer includes one or more of a photoreactive polymer and a photoreactive dye that changes from an optically transparent state to a fully occlusive state upon exposure to at least one of a plurality of light wavelengths.

In some embodiments, a light deactivated adhesive drape system is configured to be coupled to tissue, the system comprising: a drape comprising: an absorbent portion configured to contact a wound on the tissue; at least one photosensitive adhesive portion configured to adhere to the tissue and having at least one release agent disposed within the adhesive layer, wherein the at least one release agent is configured to weaken a bond of the adhesive layer to the tissue upon exposure to at least one of a plurality of light wavelengths; at least one acrylic and/or polyurethane adhesive portion configured to adhere to the tissue, the adhesion of the at least one acrylic adhesive portion having an adhesion less than the at least one photosensitive adhesive portion in an activated state; a drape cover disposed over the absorbent portion, the drape cover including: a thin, flexible, and breathable film layer, and an adhesive layer disposed on an underside of the film layer, the adhesive layer including the at least one photosensitive adhesive portion and the at least one acrylic and/or polyurethane adhesive portion; a removable blocking layer configured to block the plurality of light wavelengths that activate the at least one release agent, wherein the plurality of light wavelengths are wavelengths comprising a portion of the visible light spectrum; and a removable release layer disposed on an underside of the drape and configured to cover the adhesive layer.

In some embodiments, a method comprises coupling a light deactivated adhesive drape system to a patient's tissue; exposing the photosensitive adhesive layer to the at least one of the plurality of light wavelengths configured to weaken the bond of the adhesive layer; and removing the drape from the tissue. In some embodiments, the method further comprises removing the removable filter layer from the drape system.

The foregoing has outlined rather broadly the features and technical advantages of the present disclosure in order that the detailed description that follows may be better understood. Additional features and advantages of the disclosed embodiments will be described hereinafter that form the subject of the claims of the disclosure. It should be appreciated by those skilled in the art that the conception and specific embodiments disclosed may be readily utilized as a basis for modifying or designing other structures for carrying out the same purposes of the present disclosed embodiments. It should also be realized by those skilled in the art that such equivalent constructions do not depart from the spirit and scope of the disclosed embodiments as set forth in the appended claims. The novel features that are believed to be characteristic of the disclosed embodiments, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosed embodiments.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

In the following detailed description of the preferred embodiments, reference is made to the accompanying drawings that form a part hereof, and in which is shown by way of illustration specific preferred embodiments in which the invention can be practiced. These embodiments are described in sufficient detail to enable those skilled in the art to practice the invention, and it is understood that other embodiments can be utilized and that logical structural, mechanical, electrical, and chemical changes can be made without departing from the spirit or scope of the invention. To avoid detail not necessary to enable those skilled in the art to practice the invention, the description can omit certain information known to those skilled in the art. It is understood that reference to a feature by numeric designation does not necessarily refer only to any particular embodiment depicted in a drawing. The following detailed description is, therefore, not to be taken in a limiting sense, and the scope of the present invention is defined only by the appended claims.

The following definitions are provided to better define the present invention and to guide those of ordinary skill in the art in the practice of the present invention. Unless otherwise noted, terms are to be understood according to conventional usage by those of ordinary skill in the relevant art.

Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" can be used to describe the pressure applied to the tissue site, the actual pressure applied to the tissue site can be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

As used herein, the term "coupled" includes "indirect coupling" via a separate object. For example, a drape can be coupled to the tissue site if both the drape and the tissue site are coupled to one or more third objects, such as a release agent or a second adhesive layer. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond, and electrostatic coupling.

Various aspects of the present invention comprise a system and method for systems and methods for mitigating premature light deactivation of light deactivated adhesive drapes, a portion of which is shown in each of the FIGS. 1A-6. Various embodiments can facilitate the removal of the drape from the tissue site with less trauma to a patient than conventional drapes while preventing premature deactivation of the adhesive. The tissue site may be skin tissue, wound tissue, bone tissue, or any other type of tissue. Various embodiments of the system and method described herein comprise, or can be used with reduced or negative pressure wound healing technology.

Figure 1A:
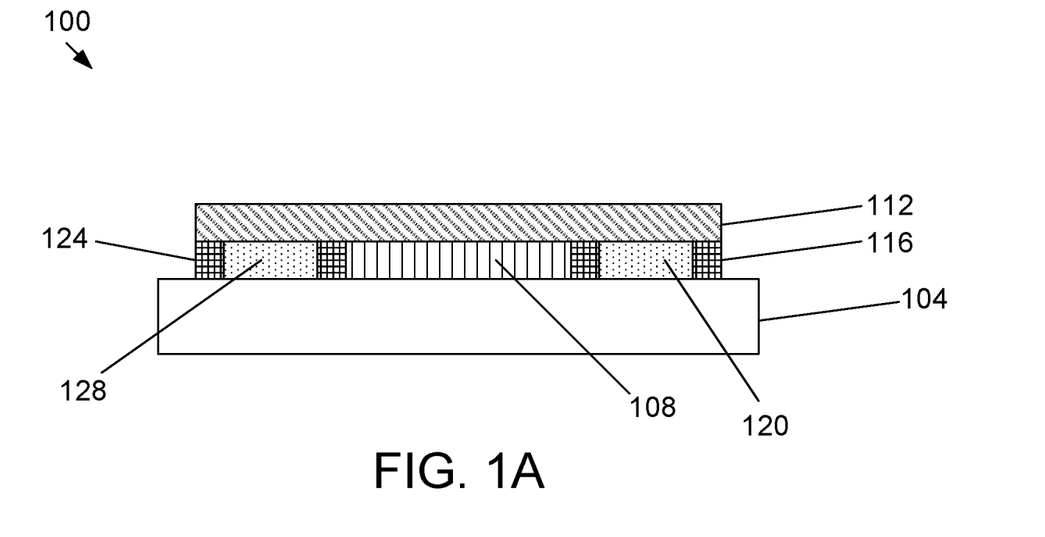
FIGS. 1A-1B are cross-sectional views of a light deactivated adhesive drape system in accordance with an illustrative embodiment of the present disclosure.
Figure 1B:
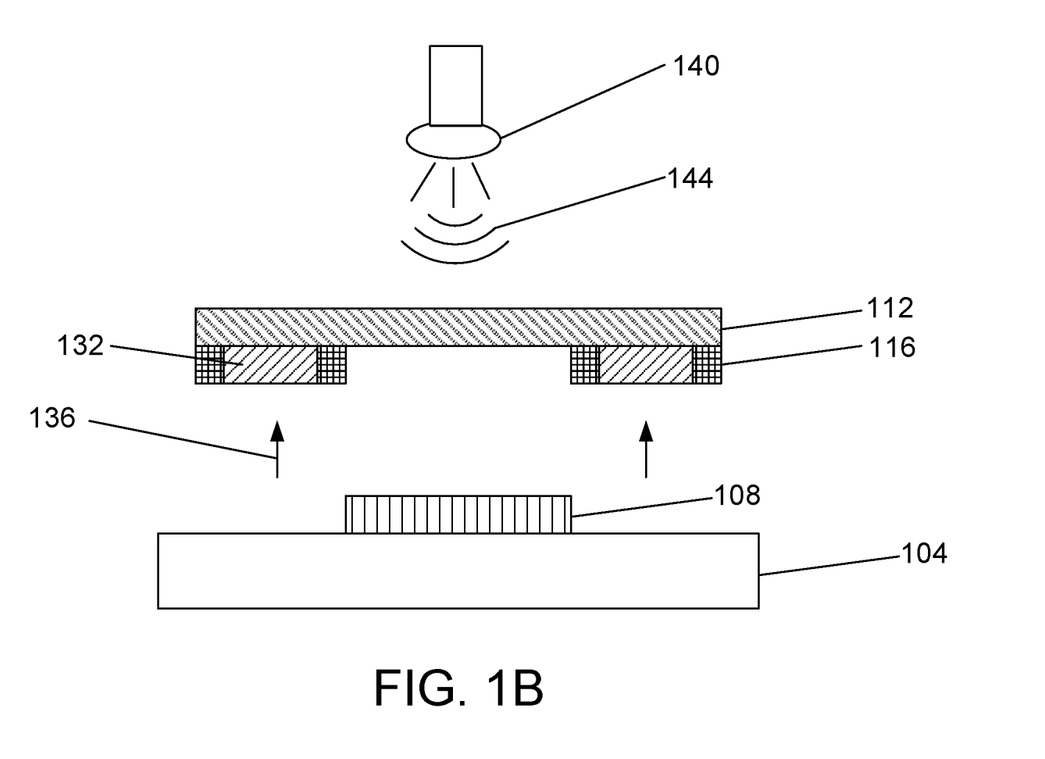

Referring more specifically to FIGS. 1A and 1B, an illustrative embodiment of a light deactivated adhesive drape system 100 disposed onto patient tissue 104 is shown. The system 100 comprises an absorbent drape portion 108, a drape cover 112, an adhesive layer 116 having at least one photosensitive adhesive portion 120 and at least one acrylic and/or polyurethane adhesive portion 124. In the embodiment shown, both adhesive portions 120 and 124 are coupled to the drape cover 112. In the embodiments shown, a drape can be generally understood to be a covering over a tissue 104 that is preferably sterilizable. A drape can comprise a biocompatible thin film material, such as a polymer, a woven or non-woven material, an elastic or non-elastic material, an occlusive or nonocclusive material, and a flexible or inflexible material. A drape can comprise an impermeable, semi-permeable, or permeable material. Permeability characteristics can be selected according to desired moisture and gas (e.g., oxygen) transmission. In some embodiments, the drape comprises a material relatively impermeable to moisture and relatively permeable to oxygen. A drape can be coated with a material, for example, to control breathability. A drape can comprise a material which allows or facilitates transmission of external stimuli, such as light, sound, moisture or heat. For example, a drape material can be semi- or substantially transparent to electromagnetic radiation, such as visible, ultraviolet (UV), or infrared light. A drape can be composed of one or more layers. In some embodiments, a drape can be a bilayer drape. As another example, three, four, or more drape layers may be used, with combinations of materials selected according to desired function.

In the embodiments shown, the absorbent portion 108 is a tissue contacting material that is therapeutic and promotes healing of a wound. The absorbent portion 108 can be a hydrophilic foam, foam and absorbent laminate, algenate, hydro-polymer, textile, and/or non-woven or bio-polymer such as a collagen. This list of absorbent materials is non-exhaustive and any suitable absorbent, protective, and therapeutic material can be used. In the embodiments shown, the absorbent portion 108 can form a central island in the drape system 100 about which the adhesive layer 116 is used to fixate the absorbent material to the patient for the benefit of the wound and management of fluids.

In the embodiments shown, drape cover 112 is placed over absorbent portion 108. In the embodiments shown, adhesive layer 116 comprising photosensitive adhesive portions 120 and acrylic and/or polyurethane adhesive portions 124 on its underside (skin/island facing side). In the embodiments shown, acrylic and/or polyurethane adhesive portions 124 can be used to hold the drape system 100 together. In the embodiments shown, adhesive layer 116 extends around the border of the island of absorbent material 108 and is used to affix the AWD to a patient. In the embodiments shown, adhesive layer 116 can be pattern printed to provide areas of adhesive and areas without adhesive where greater MVTR can allow for improved evaporation from the absorbent material 108. Both the drape cover 112 and adhesive layer 116 should not impede the transmission of the appropriate wavelengths and intensities of light required to activate and cause the switching of the photosensitive adhesive portions 120. In some embodiments, it may be optimal if the drape cover 112 and adhesive layer 116 are optically transparent. In some embodiments, the drape cover 112 and/or adhesive layer 116 may be tinted with a color. In these embodiments, the tint color should not disrupt the passage of the appropriate wavelengths and intensities of light required to activate and cause the switching of the photosensitive adhesive portions 120.

In the embodiment shown, the drape cover 112 may be a breathable and/or semiporous film such as polyurethane or a thin foam but other suitable materials may be used. There are a range of materials which the drape cover 112 can be formulated from although they generally need to be thin, flexible and have a moderate to high MVTR. The adhesive layer 116 adheres to the tissue 104 thereby coupling the drape cover 112 to the tissue 104. The drape cover 112 may cover any portion of the absorbent portion 108, the adhesive layer 116, and the tissue 104 as may be required.

The adhesive portions 124 can comprise one or more materials including, but not limited to, polyurethane, acrylic (e.g., cyanoacrylate), hydrogel, silicon or silicone based material, natural rubber, synthetic rubber, styrene block copolymers, polyvinyl ethers, poly(meth)acrylates, polyolefins, hydrocolloid (e.g., a rubber based hydrocolloid), or a combination thereof. In some embodiments, the adhesive portions 124 comprises a polymer or co-polymer. For example, the adhesive portions 124 can comprise a co-polymer of polyurethane and silicone or various acrylic co-polymers.

The photosensitive adhesive portions 120 may include at least one release agent 128 comprising a release material. In the embodiment shown, photosensitive adhesive portions 120 have a plurality of release agents 128 (represented by dots). The release agent 128 can physically or chemically affect adhesion characteristics between a drape and a tissue 104. A release agent 128 can comprise a variety of molecular compositions depending on the particular embodiment being implemented, including but not limited to a photopolymer, an oil particle, a gas particle, a solvent, a lipid, and/or one or more microstructures. Release agents 128 can be present in an inert or inactive form in, on, or near adhesive portions 120. For example, a release agent 128 can be mixed with the adhesive; on the surface of the adhesive with a random or patterned coverage; coupled to the drape with a random or patterned coverage; or contained within a microstructure located in these or other locations. Upon release or activation, release agents 128 can migrate within the adhesive portions 120 or along an interface between adhesive portions 120 and a tissue 104 to facilitate the removal of a drape affixed thereto. In the embodiment shown, the release agent 128 is configured to transition from an unreleased state (shown in FIG. 1A) to a release state 132 (represented by diagonal lines in FIG. 1B) to weaken a bond of adhesive portions 120 to the tissue 104 upon exposure to an external stimulus. Various external stimulus can be employed depending on the particular embodiment being implemented. Non-limiting examples of the external stimulus include electromagnetic (e.g., UV, visible, or infrared light), magnetic, sound, pH, pressure (e.g., positive atmospheric pressure, negative atmospheric pressure, shear force, direct force), thermal, moisture, or a substance. The external stimulus can also be a substance, compound, liquid, or gas capable of reacting with a release agent 128 in adhesive portions 120 such that the release agent 128 transitions from an unreleased state to a released state. In the embodiment shown, the external stimulus is one or more of a plurality of light wavelengths. The weakened bond that occurs as a result of the release of release agent 128 allows a user of the light deactivated adhesive drape system 100 to apply an upward force on drape cover 112, such as a force indicated by arrow 136, to remove drape cover 112 from tissue 104. The weakened bond reduces the stress applied to tissue 104 in the removal of drape cover 112 from tissue 104. Thus, a patient feels less pain and discomfort when the drape cover 112 is removed. A residue of molecules from adhesive layer 116 might remain on tissue 104 after removal of drape cover 112 depending on a variety of factors such as the type of release agent used.

Referring more specifically to FIG. 1A, in the embodiment shown, release agents 128 are inertly dispersed within adhesive portions 120 and can be located anywhere within adhesive portions 120, as well as any of the outer surfaces of adhesive portions 120, such as an interface between adhesive portions 120 and drape cover 112. In some embodiments, release agents 128 can be bonded or coupled directly to drape cover 112, and a separate film layer (not shown in FIG. 1A), can separate release agents 128 from adhesive portions 120. In these embodiments, the presence of an external stimulus can weaken, break-down, or increase the permeability of the separate film layer such that release agents 128 are allowed to migrate into adhesive portions 120 to facilitate the removal of drape cover 112 from tissue 104. As shown in FIG. 1B, release agents 128 may be released in the presence of external stimulus such that release agents 128 are allowed to migrate within adhesive portions 120 and the interface between adhesive portions 120 and tissue 104. In the embodiment shown, a light source 140 exposes drape cover 112 and adhesive layer 116 to a plurality of light wavelengths 144. The light source 140 can be a UV light source or a light source that emits visible light wavelengths. In some embodiments, exposure to the plurality of light wavelengths 144 can cause microstructures containing release agents 128 to rupture or tear, thereby releasing release agents 128 from the interior of the microstructures. These released release agents 128 can then be interspersed into adhesive portions 120 and the interface between adhesive portions 120 and tissue 104, thereby weakening the bond between drape cover 112 and tissue 104 and facilitating the removal of drape cover 112 from tissue 104. As the plurality of light wavelengths 144 reach adhesive portions 120, release agents 128 may transition from an unreleased state (as shown in FIG. 1A) to a released state 132 (as shown in FIG. 1B) as they are exposed to the plurality of light wavelengths 144. In embodiments where the plurality of light wavelengths 144 are UV wavelengths, the UV wavelengths may be within a range of 280 nm-395 nm, although it may be preferable to have the UV wavelengths be UVA wavelengths within a range of 315 nm-395 nm. In embodiments where the plurality of light wavelengths 144 are visible light wavelengths, the visible light wavelengths may be within a range of 400 nm-700 nm, although it may be preferable to have the visible light wavelengths be wavelengths within a range of 400 nm-500 nm. In some embodiments, the photosensitive adhesive portions 120 can be optimized to deactivate in <5 minutes of exposure to a range of ambient light levels, wavelengths, and intensities ranging from environments such as a domestic location with artificial light bulbs (e.g., hospital wards) and strong outdoor light. In some embodiments, the intensity of the light source may affect the time it takes for the switchable adhesive to deactivate (i.e., the deactivation time may be less when the intensity of the light is higher such as when exposed to outdoor sunlight vs. indoor ambient light). Switchable adhesives with other deactivation times may be used, such as times within a range of 30 seconds to 6 minutes.

Figure 2A:
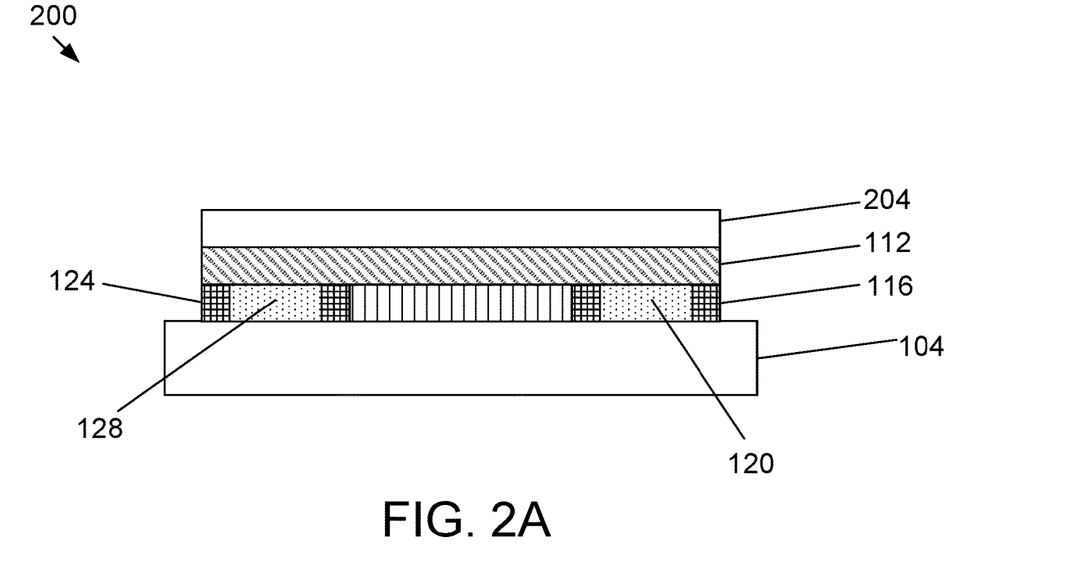
FIGS. 2A-2C are cross-sectional views of a light deactivated adhesive drape system in accordance with another illustrative embodiment of the present disclosure.
Figure 2B:
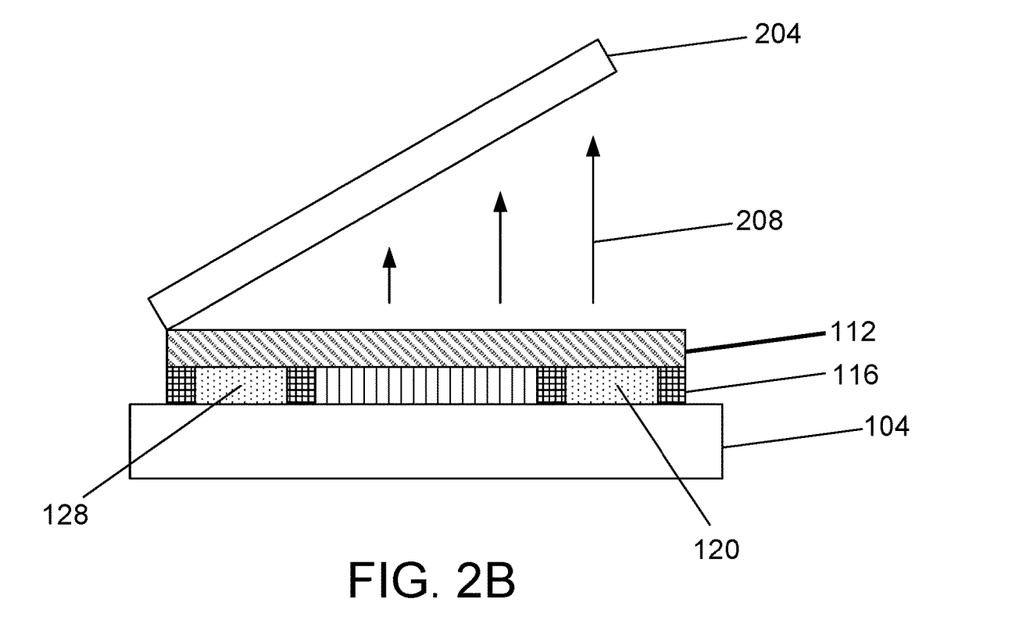
Figure 2C:
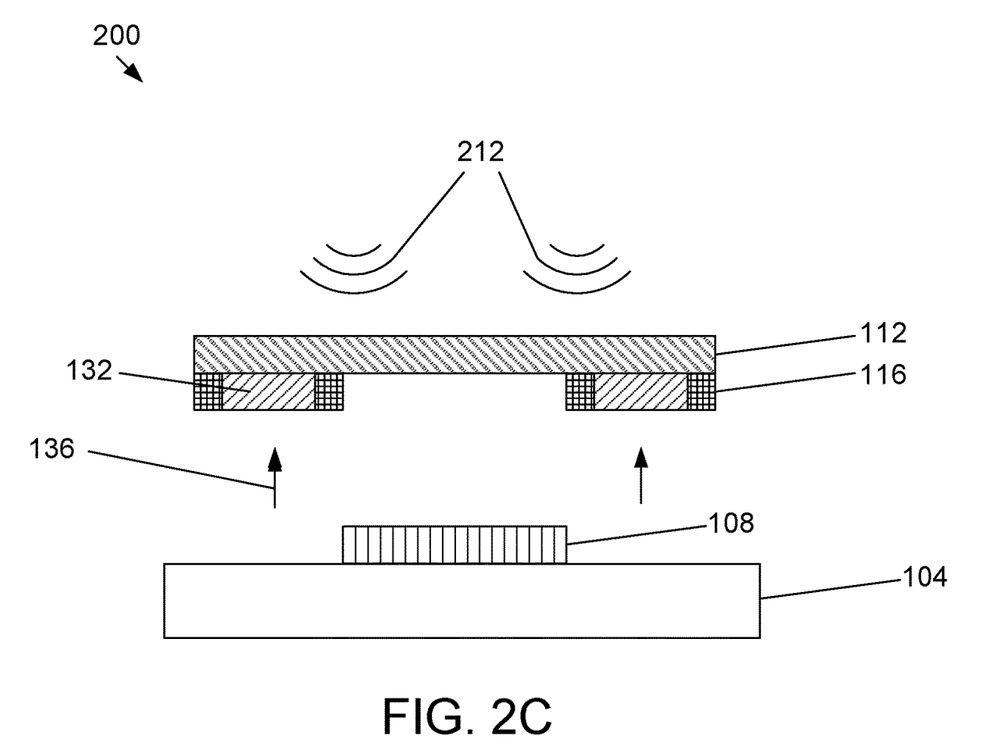

Referring now to FIGS. 2A-2C, another illustrative embodiment of a light deactivated adhesive drape system 200 disposed onto patient tissue 104 is shown. In this embodiment, light deactivated adhesive drape system 200 is configured to release adhesive portions 120 upon exposure to ambient, visible light instead of UV light. Although having adhesive portions 120 release upon exposure to visible light is advantageous in that it doesn't require a specific UV light source and enables release to occur in any environment having ambient light, it also can increase a likelihood that the adhesive portions 120 will prematurely deactivate. In order to prevent premature deactivation, the adhesive portions 120 may be constructed with release agents 128 that only release upon exposure to certain wavelengths of visible light. For example, in some embodiments, release agents 128 will only transition to a released state 132 when exposed to visible light wavelengths in the blue and violet portions of the visible light spectrum. In the embodiment shown, a blocking layer 204 is disposed over drape cover 112 of the drape. In this embodiment, blocking layer 204 is configured to block the visible light wavelengths that release the adhesive portions 120 while allowing other visible light wavelengths to pass through. For example, when exposed to visible light, blocking layer 204 will block the blue and violet wavelengths but allow the red, orange, yellow, and/or green wavelengths to pass through. In this way, blocking layer 204 can be partially transparent and enables a clinician or a nurse to visually inspect the drape and the wound site without premature deactivation of the adhesive portions 120. In other embodiments, blocking layer 204 can be opaque and/or partially or fully light occlusive. In some embodiments, blocking layer 204 is a colored layer that contains a dye or other coloring agent corresponding to one or more colors of the visible light spectrum that have wavelengths that do not deactivate the adhesive portions 120 (e.g., red, orange, yellow, and/or green). In some embodiments, blocking layer 204 is a photo-reactive polymer or can incorporate a photo-reactive dye such that blocking layer 204 is transparent when exposed to light of a wavelength/intensity insufficient to deactivate the switchable adhesive but becomes fully light occlusive when exposed to light of a wavelength/intensity sufficient to trigger the deactivation the switchable adhesive.

In the embodiment shown in FIG. 2B, blocking layer 204 is configured to be removable. This enables the adhesive portions 120 to be deactivated at a time a user desires to remove the drape from tissue 104. In some embodiments, the blocking layer 204 can be a printed layer printed directly onto the drape cover 112 or the adhesive portions 120. In other embodiments, blocking layer 204 can be a peelable layer that adheres to the outer surface of drape cover 112. In the embodiment shown, blocking layer 204 can cover the entire surface of drape cover 112. In other embodiments, blocking layer 204 can cover only the surfaces of drape cover 112 over adhesive portions 120. When removal of the drape from tissue 104 is desired, a user of the light deactivated adhesive drape system 200 can apply a force on blocking layer 204, such as a force indicated by arrows 208, to remove blocking layer 204 from drape cover 112. As shown in FIG. 2C, once the blocking layer 204 has been removed, the adhesive portions 120 can be exposed to deactivation wavelengths (e.g., ambient light 212) that comprises light wavelengths configured to deactivate adhesive portions 120. Upon exposure to ambient light 212, release agents 128 can transition from an unreleased state to a released state 132. The drape including drape cover 112 can then be removed from tissue 104. If any residue of adhesive portions 120 remains on tissue 104 after removal of the drape, it may be removed.

In some embodiments, blocking layer 204 is a frequency/intensity/UV blocking film layer which may be transparent or fully occlusive. Transparency will depend on the ability of the selected material to completely and totally block any activating wavelengths from the switchable adhesive under all light and environmental conditions. This material should optimally be highly breathable with a high MVTR. It can also incorporate an adhesive that may be acrylic, polyurethane, or other suitable material; however, the bond strength should be tuned such that the material is retained in its position but requires approximately 1-2 N in order to remove layer. In some embodiments, blocking layer 204 may include printing or may be colored such that it provides indication to a user of the system that the blocking layer 204 should not be removed until removal of the drape is desired and deactivation of the switchable adhesive is necessary. In some embodiments, blocking layer 204 can be disposed over the entire surface area of drape cover 112. In other embodiments, blocking layer 204 may only be aligned and fitted to surface areas of drape cover 112 where the switchable adhesive portions 120 are located. In some embodiments, blocking layer 204 may be a printed/coated dye/particulate layer that is printed over the photosensitive adhesive portions 120 to prevent premature deactivation.

Figure 3A:
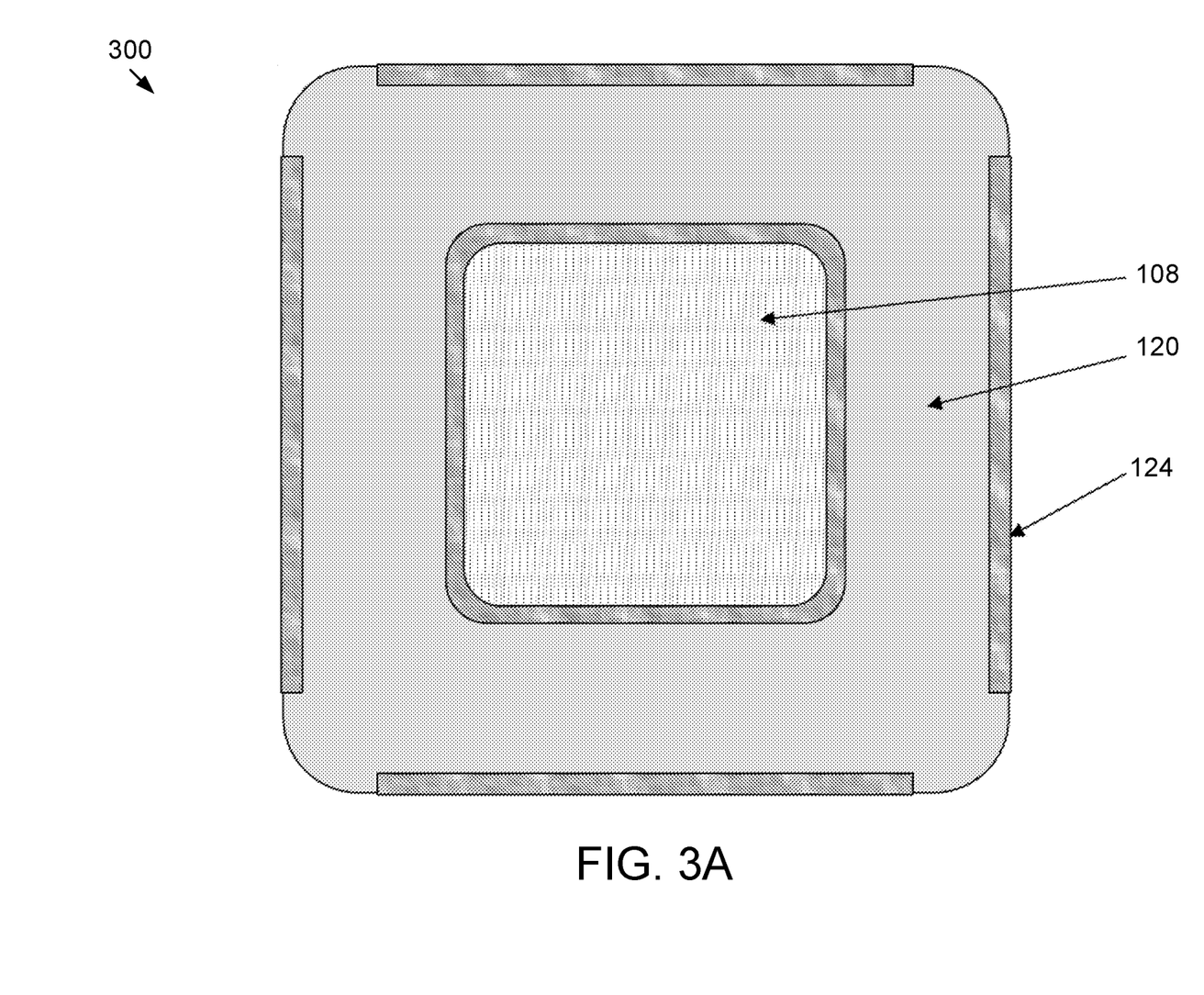
FIGS. 3A-3B are various views of the light deactivated adhesive drape system disclosed in FIGS. 2A-C.
Figure 3B:
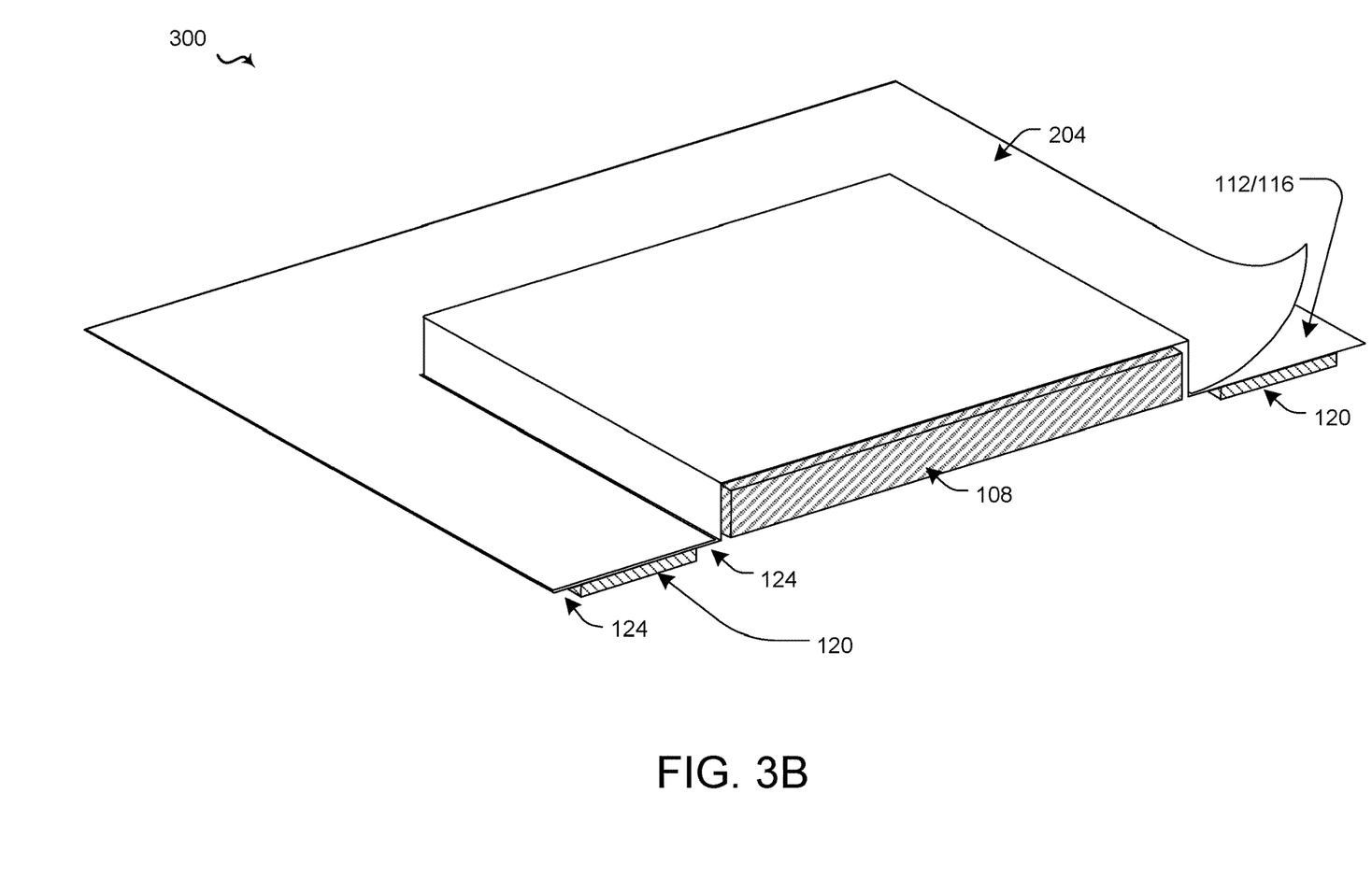

Referring now to FIGS. 3A-3B, another illustrative embodiment of a light deactivated adhesive drape system 300 disposed onto patient tissue 104 is shown. Although the embodiments shown depict a drape system that is square-shaped, the drape system may be different shapes and forms for different anatomical locations. FIG. 3A shows a top view of drape system 300, which includes a drape having an absorbent portion 108, photosensitive adhesive portions 120, and acrylic and/or polyurethane adhesive portions 124. In the embodiment shown, absorbent portion 108 is disposed at the center of the drape and comprises a central "island." Photosensitive adhesive portions 120 and acrylic and/or polyurethane adhesive portions 124 are disposed in adhesive layer 116 of drape cover 112 that completely surrounds the central island of absorbent portion 108.

In some embodiments, photosensitive adhesive portions 120 are comprised of a 100 to 250 GSM light-switchable adhesive material. In the embodiment shown, photosensitive adhesive portion 120 is set inboard of both the central island absorbent portion 108 and inboard of the outer edges of the drape such that there are acrylic and/or polyurethane adhesive portions 124 of traditional adhesive bordering each side of the photosensitive adhesive portion 120. In the embodiment shown, one adhesive portion 124 completely surrounds the border of the central island absorbent portion 108. In the embodiment shown, other adhesive portions 124 are disposed on each side of the drape at the edges of the drape. In some embodiments, discontinuous areas of traditional acrylic adhesive 124 can be disposed on either or both the border between the photosensitive adhesive portion 120 and the central island absorbent portion 108 and/or the edges of the drape such that low-level tissue adhesion can be achieved without continuous areas of adhesive portions 124.

In some embodiments, adhesive portions 124 can be narrow strips and/or circular or other suitably shaped areas and may be visible and able to adhere to tissue 104 on each side of the adhesive portion 120. This configuration can allow the drape to remain held in place after the photosensitive adhesive portions 120 have been deactivated but enables the drape to be removed without trauma to the tissue. This configuration can allow the drape to be assembled and maintain structural integrity before and after use and also prevents a full and potentially heavy drape from prematurely falling off the tissue once photosensitive adhesive portions 120 have been deactivated. In the embodiment shown, removable blocking layer 204 is positioned over the top surface of the drape above the areas of adhesive portions 120 and 124.

In some embodiments, the drape system 300 can provide feedback to a user of the drape system when the photosensitive adhesive portions 120 have been deactivated. In the embodiment shown, the photosensitive adhesive portions 120 extend to the outer edges of the drape at each corner. This configuration enables the user can use a finger to roll up an edge of the drape after removal of the blocking layer 204. Once switched, the photosensitive adhesive portions 120 will readily give way and the user can then use one or more of the corners of the drape to grip the drape for removal. In some embodiments, printing may be disposed on the drape cover 112 that is revealed once the blocking layer 204 is removed. The drape underneath blocking layer 204 may also include printing to remind the user to wait for the time needed for the photosensitive adhesive portions 120 to fully deactivate (e.g., 5 minutes) in order to prevent premature removal of the drape and possible trauma to the tissue. In other embodiments, a light sensitive dye can be triggered to become visible as the switchable adhesive becomes deactivated such that an indicator can be provided to the user when the adhesive is deactivated. This could be a change in general color and/or the revealing of a symbol or test.

FIG. 3B shows a perspective view of drape system 300, showing absorbent portion 108, drape cover 112, adhesive layer 116, photosensitive adhesive portions 120, and acrylic and/or polyurethane adhesive portions 124, and blocking layer 204. In the embodiment shown, blocking layer 204 is disposed over the entire surface area of drape cover 112, including over absorbent portion 108. In other embodiments, blocking layer 204 may only be aligned and fitted to surface areas of drape cover 112 where the switchable adhesive portions 120 are located. In the embodiment shown, blocking layer 204 is configured to be peeled off the drape cover 112 to expose the photosensitive adhesive portions 120 to deactivating light wavelengths/intensities when removal of the drape is desired. Once the photosensitive adhesive portions 120 are deactivated, acrylic and/or polyurethane adhesive portions 124 keep the drape adhered to the patient tissue to prevent the drape from falling off.

Figure 4:
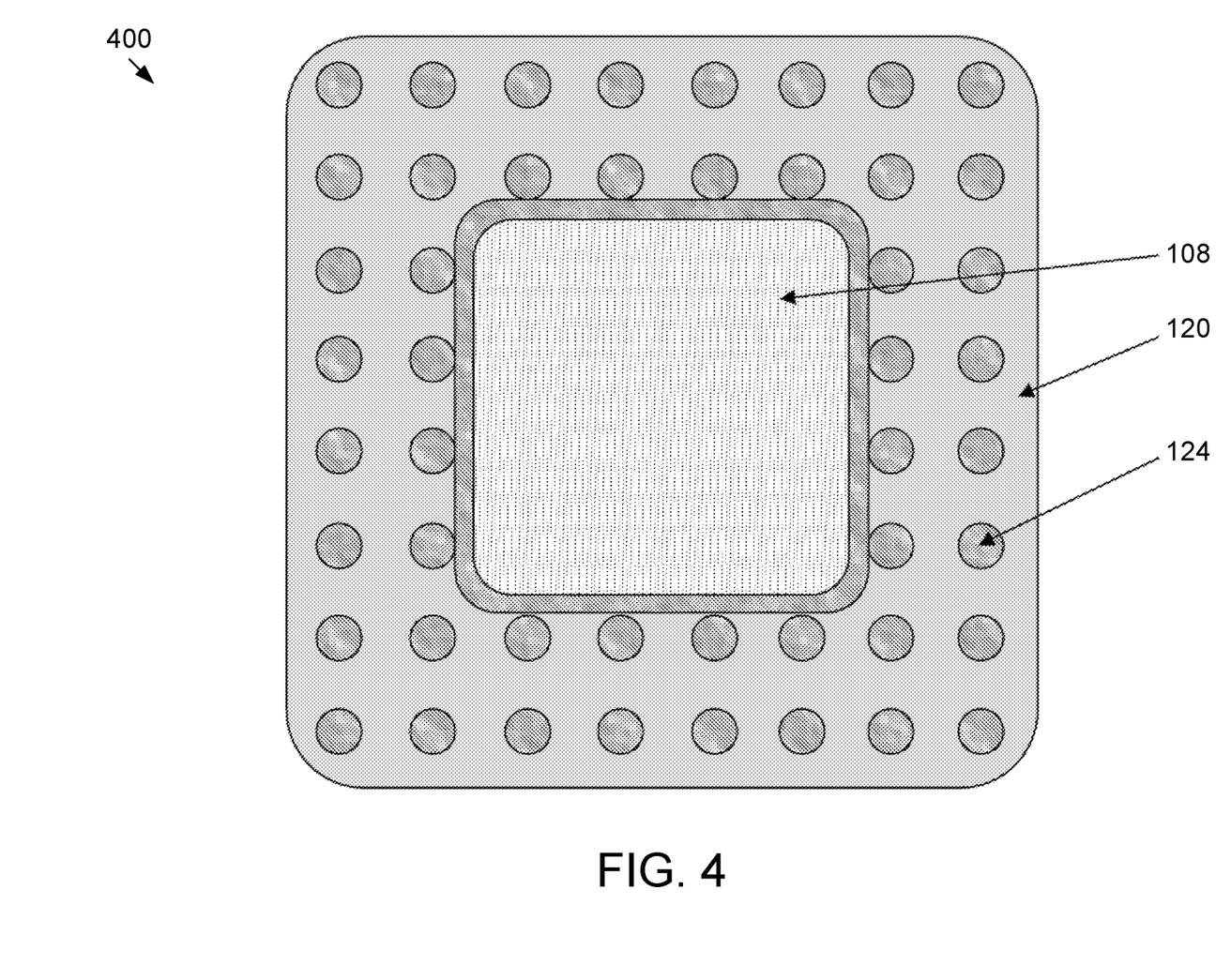
FIG. 4 is a top-down view of a light deactivated adhesive drape system in accordance with another illustrative embodiment of the present disclosure.

Referring now to FIG. 4, another illustrative embodiment of a light deactivated adhesive drape system 400 disposed onto patient tissue 104 is shown. Similar to drape system 300, drape system 400 has a drape with an absorbent portion 108, photosensitive adhesive portions 120, and acrylic and/or polyurethane adhesive portions 124. However, in the embodiment shown, instead of adhesive strips disposed along each side edge of the drape, photosensitive adhesive portion 120 is perforated with a plurality of islands/portions of acrylic and/or polyurethane adhesive 124 that will hold the dressing in place with a low tack once the switchable adhesive has been deactivated. In the embodiment shown, the blocking layer 204 may be absent over the acrylic and/or polyurethane adhesive portions 124. In other embodiments, the blocking layer 204 may be solid over the entire surface of drape cover 112, obscuring the perforations. Having these perforations may also improve skin breathability in the locale of the photosensitive adhesive portions 120 as there will be one fewer layer of adhesive in some selected locations. The more adhesive/more layers of adhesive which are present, the less breathability will exist unless the adhesive formulation is modified to include an absorber. In some embodiments, the locations of the adhesive potions may vary; however, the durable bond adhering the drape to the tissue during wound treatment is achieved by the photosensitive adhesive portions 120, not the acrylic and/or polyurethane adhesive portions 124. In some embodiments, the ratio of the amount/number of photosensitive adhesive portions 120 to the acrylic and/or polyurethane adhesive portions 124 disposed in the adhesive layer 116 is 80:20. In some embodiments, the ratio of adhesive tack of the photosensitive adhesive portions 120 to the acrylic and/or polyurethane adhesive portions 124 is 50:50.

Figure 5:
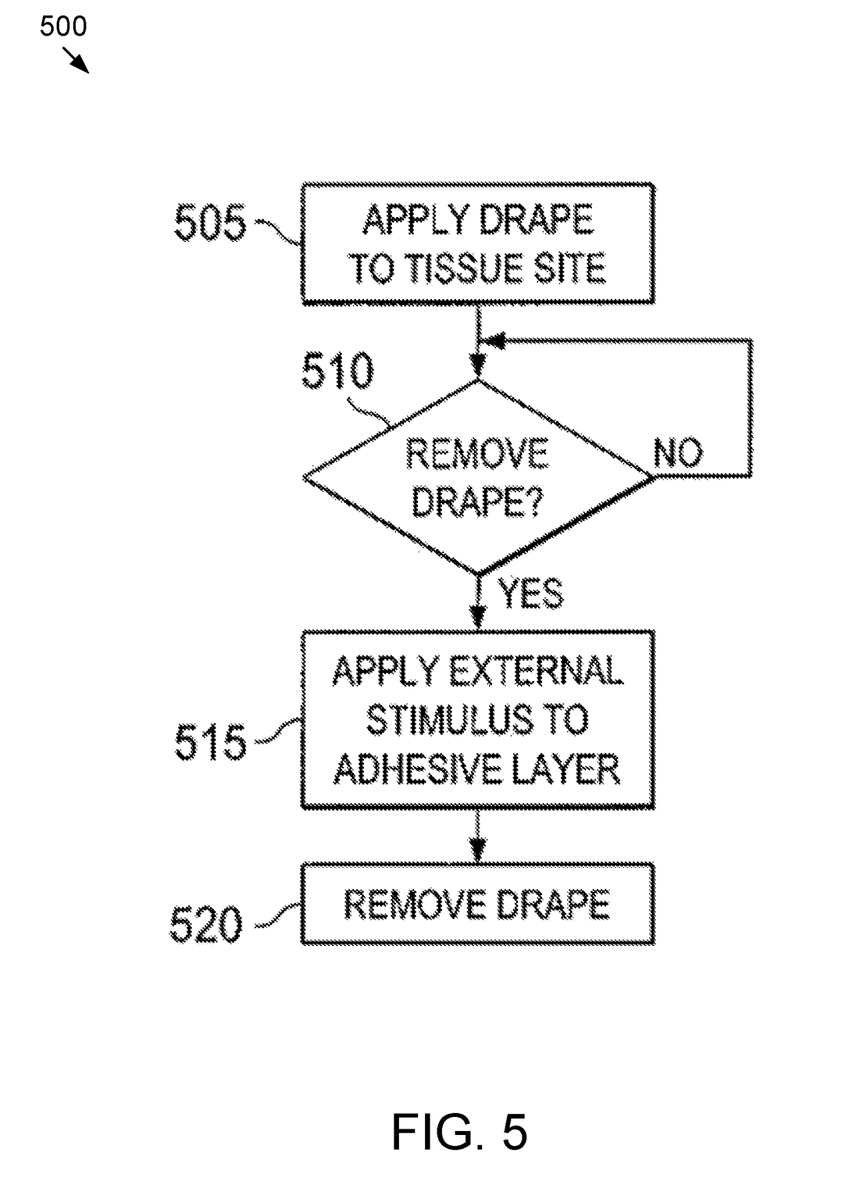
FIG. 5 is a flowchart illustrating a process for using a light deactivated adhesive drape system in accordance with an illustrative embodiment of the present disclosure.

FIG. 5 depicts a flowchart illustrating a general process 500 for facilitating removal of a light deactivated adhesive drape system from a tissue 104 in accordance with an illustrative embodiment of the disclosure. The process illustrated in FIG. 5 can be implemented by a user of a reduced or negative pressure treatment system. The process begins by applying a drape to a tissue 104 (step 505). In this step, adhesive portions 120 can bind to the tissue 104. Also in this step, reduced or negative pressure can be applied to the tissue 104 using a reduced or negative pressure treatment system. The process determines whether to remove the drape from the tissue 104 (step 510). If the process determines not to remove the drape from the tissue 104, the process returns to step 510. If the process determines to remove the drape from the tissue 104, the process applies an external stimulus to the drape, including the adhesive portions 120 coupled to the drape (step 515). In this step, a release agent 128 can be released in accordance with any of the illustrative embodiments described above to facilitate the removal of the drape from the tissue 104. The process then removes the drape from the tissue 104 (step 520).

Figure 6:
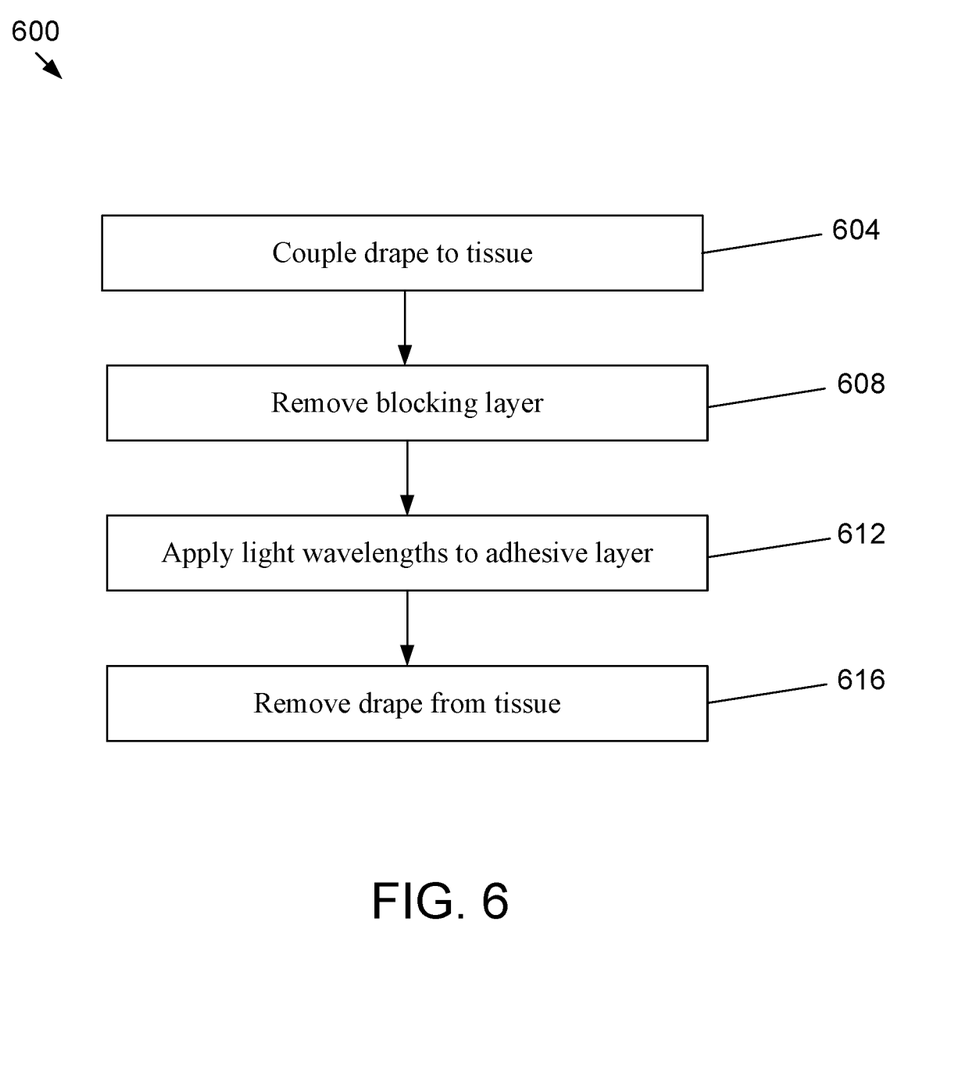
FIG. 6 is a flowchart illustrating a process for using a light deactivated adhesive drape system in accordance with another illustrative embodiment of the present disclosure.

FIG. 6 depicts a flowchart illustrating process 600 for facilitating removal of a light deactivated adhesive drape system from a tissue 104 in accordance with an illustrative embodiment of the disclosure. Referring to FIG. 6, process 600 begins by coupling a drape to a tissue (step 604). In this embodiment, the drape may have a removable blocking layer similar to layer 204 discussed above. Process 600 continues by, when the drape is desired to be removed, the blocking layer is removed to expose the photosensitive adhesive layer to light (step 608). Process 600 continues by applying certain deactivating light wavelengths to the photosensitive adhesive layer to deactivate the adhesive (step 612). The process then enables a removal of the drape from the tissue (step 616).

The flowcharts and block diagrams in the different depicted embodiments illustrate the architecture, functionality, and operation of some possible implementations of the apparatus and methods. In some alternative implementations, the function or functions noted in the block can occur out of the order noted in the figures. For example, in some cases, two blocks shown in succession can be executed substantially concurrently, or the blocks can sometimes be executed in the reverse order, depending upon the functionality involved.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A light deactivated adhesive drape system configured to be coupled to tissue, the light deactivated adhesive drape system comprising:
   a drape comprising:
      an absorbent portion configured to contact a wound on the tissue;
      at least one photosensitive adhesive portion configured to adhere to the tissue and having at least one release agent disposed within an adhesive layer, wherein the at least one release agent is configured to weaken a bond of the adhesive layer to the tissue upon exposure to at least one of a plurality of light wavelengths, the at least one photosensitive adhesive portion extending to outer edges of the drape;
      a plurality of acrylic and/or polyurethane adhesive portions configured to adhere to the tissue, the plurality of acrylic and/or polyurethane adhesive portions perforating the at least one photosensitive adhesive portion, the plurality of acrylic and/or polyurethane adhesive portion having an adhesion less than the at least one photosensitive adhesive portion in an activated state and greater than the at least one photosensitive adhesive portion in a deactivated state,
   wherein the plurality of acrylic and/or polyurethane adhesive portion maintains adhesion to the tissue upon exposure to the at least one of a plurality of light wavelengths; and
   a removable blocking layer configured to block the plurality of light wavelengths that activate the at least one release agent, and the plurality of acrylic and/or polyurethane adhesive portions are not covered by the removable blocking layer.

2. The light deactivated adhesive drape system of claim 1, further comprising a drape cover disposed over the absorbent portion, the drape cover including:
   a thin, flexible, and breathable film layer; and
   the adhesive layer disposed on an underside of the thin, flexible, and breathable film layer, the adhesive layer including the at least one photosensitive adhesive portion and plurality of acrylic and/or polyurethane adhesive portion.

3. The light deactivated adhesive drape system of claim 2, wherein:
   the drape cover is configured to enable the plurality of light wavelengths to pass through the drape cover and contact the at least one photosensitive adhesive portion;
   the drape cover is optically transparent;
   the thin, flexible, and breathable film layer comprises a material having a moderate to high moisture vapor transmission rate (MVTR); and
   the thin, flexible, and breathable film layer is disposed on top of the absorbent portion and the adhesive layer and extends across an entire surface area of the drape.

4. The light deactivated adhesive drape system of claim 1, further comprising a removable blocking layer configured to block the plurality of light wavelengths that activate the at least one release agent, wherein the plurality of light wavelengths are wavelengths comprising a portion of the visible light spectrum.

5. The light deactivated adhesive drape system of claim 4, wherein:
   the removable blocking layer comprises a material having a high MVTR;
   the removable blocking layer includes an adhesive having a bond strength enabling it to be removed with an application of 1-2 N of force;
   the removable blocking layer covers a top of the adhesive layer, the absorbent portion, or both;
   the removable blocking layer includes an indication to a user of the drape that the removable blocking layer should be removed when deactivation of the at least one photosensitive adhesive portion is desired; or
   a combination thereof.

6. The light deactivated adhesive drape system of claim 1, further comprising a removable release layer disposed on an underside of the drape and configured to cover the adhesive layer.

7. The light deactivated adhesive drape system of claim 1, wherein:
   the absorbent portion is disposed in a central area of the drape and comprises one or more of a hydrophilic foam, foam and absorbent laminate, algenate, hydropolymer, textile, non-woven polymer, and bio-polymer;
   the adhesive layer is pattern printed to define adhesive areas and non-adhesive areas; and
   one of the non-adhesive areas covers the absorbent portion and the adhesive areas completely surround the absorbent portion.

8. The light deactivated adhesive drape system of claim 1, wherein the drape includes an indication to a user of the drape that the at least one photosensitive adhesive portion is deactivated upon exposure to the at least one of a plurality of light wavelengths.

9. The light deactivated adhesive drape system of claim 8, wherein the indication is a light sensitive dye that changes color, state, or design upon deactivation of the at least one photosensitive adhesive portion.

10. The light deactivated adhesive drape system of claim 1, wherein a ratio of the at least one photosensitive adhesive portion and the plurality of acrylic and/or polyurethane adhesive portion disposed in the adhesive layer is 80:20.

11. The light deactivated adhesive drape system of claim 1, wherein the removable blocking layer includes one or more of a printed layer, a coated dye layer, and a particulate layer.

12. The light deactivated adhesive drape system of claim 1, wherein the removable blocking layer includes one or more of a photoreactive polymer and a photoreactive dye configured to change from an optically transparent state to a fully occlusive state upon exposure to at least one of a plurality of light wavelengths.

13. A method comprising:
coupling the light deactivated adhesive drape system of claim 1 to the tissue of a patient;
exposing the at least one photosensitive adhesive portion to the at least one of the plurality of light wavelengths configured to weaken the bond of the adhesive layer; and
removing the drape from the tissue.

14. The method of claim 13, further comprising removing the removable blocking layer from the light deactivated adhesive drape system.

* * * * *